United States Patent
Pereira Ramos et al.

(10) Patent No.: US 11,786,762 B2
(45) Date of Patent: Oct. 17, 2023

(54) PRESERVATIVE SYSTEMS FOR ORAL CARE COMPOSITIONS

(71) Applicant: Colgate-Palmolive Company, New York, NY (US)

(72) Inventors: Sandra Pereira Ramos, Sao Paulo (BR); Luiz Alberto Goncalves Filho, Sao Paolo (BR); Fernanda Correa, Sao Paolo (BR); Tatiana Cinquetti, Sao Paulo (BR); Paulo Focassio, Sao Paulo (BR)

(73) Assignee: Colgate-Palmolive Company, New York, NY (US)

(*) Notice: Subject to any disclaimer, the term of this patent is extended or adjusted under 35 U.S.C. 154(b) by 407 days.

(21) Appl. No.: 16/746,148

(22) Filed: Jan. 17, 2020

(65) Prior Publication Data

US 2020/0246643 A1 Aug. 6, 2020

Related U.S. Application Data

(60) Provisional application No. 62/799,856, filed on Feb. 1, 2019.

(51) Int. Cl.
*A61Q 11/00* (2006.01)
*A61K 8/34* (2006.01)
*A61K 8/368* (2006.01)
*A61K 8/44* (2006.01)
*A61K 8/81* (2006.01)

(52) U.S. Cl.
CPC ............. *A61Q 11/00* (2013.01); *A61K 8/345* (2013.01); *A61K 8/368* (2013.01); *A61K 8/44* (2013.01); *A61K 8/8111* (2013.01); *A61K 8/8129* (2013.01); *A61K 2800/30* (2013.01); *A61K 2800/92* (2013.01)

(58) Field of Classification Search
CPC .................................. A61K 8/44; A61Q 11/00

USPC .......................................................... 424/54
See application file for complete search history.

(56) References Cited

U.S. PATENT DOCUMENTS

| | | | |
|---|---|---|---|
| 3,703,578 A * | 11/1972 | Celia et al. .............. | A61K 8/86 424/49 |
| 9,579,269 B2 * | 2/2017 | Mello ...................... | A61K 8/19 |
| 9,795,554 B2 | 10/2017 | Brown et al. | |
| 2012/0237455 A1 | 9/2012 | Trivedi et al. | |
| 2013/0224126 A1 * | 8/2013 | Lewus .................... | A61K 8/347 424/52 |
| 2015/0290112 A1 * | 10/2015 | Nesta ..................... | A61K 8/345 424/401 |

FOREIGN PATENT DOCUMENTS

| | | |
|---|---|---|
| CN | 108186541 | 6/2018 |
| WO | 1994/016674 | 8/1994 |
| WO | 2012/023936 | 2/2012 |
| WO | 2012/064338 | 5/2012 |
| WO | 2018/033211 | 2/2018 |
| WO | 2018/156545 | 8/2018 |

OTHER PUBLICATIONS

Community Dentist Network, "How Much Mouthwash Should Someone Use." 123Dentist.com. Published Aug. 3, 2013; 5 pages. (Year: 2013).*
CN108186541, Nano Shenfeng Fujian Personal Care Products Co Ltd., "Mouth wash with multiple effects and preparation method thereof," Jun. 22, 2018, English language machine translation of abstract, Espacenet, date obtained: Jul. 21, 2020, 1 page <https://worldwide.espacenet.com/patent/search/family/062595971/publication/CN108186541A?q=CN108186541>.

* cited by examiner

*Primary Examiner* — Walter E Webb

(57) ABSTRACT

Disclosed herein are oral care compositions comprising: an orally acceptable vehicle comprising greater than about 50 wt. % water; and a preservative system comprising: benzyl alcohol, benzoic acid or a salt of benzoic acid; and an alkylene glycol. Methods of making and using these compositions are also described herein.

6 Claims, No Drawings

PRESERVATIVE SYSTEMS FOR ORAL CARE COMPOSITIONS

CROSS-REFERENCE TO RELATED PATENT APPLICATION

The present application claims the benefit of priority from U.S. Provisional Application Ser. No. 62/799,856, filed Feb. 1, 2019, the contents of which are hereby incorporated herein in their entirety.

BACKGROUND

Preservative systems play a critical role in oral care formulation development. While many preservatives are able to provide the necessary anti-microbial effect, many preservatives can have undesirable effects and can also impact the flavor profile of a composition. Thus, formulators are presented with the challenge of identifying safe preservative systems which provide an acceptable level of preservation without adversely impacting the flavor profile or stability of the composition.

Embodiments of the present invention are designed to address these, and other, needs.

BRIEF SUMMARY

In some embodiments, the present invention provides an oral care composition comprising an orally acceptable carrier comprising greater than about 50 wt. % water; and a preservative system comprising: benzyl alcohol, benzoic acid or a salt of benzoic acid; and an alkylene glycol. Some embodiments further comprise a basic amino acid in free or salt form. In some embodiments, the preservative system is substantially free of isothiazolinones.

Other embodiments provide A mouthwash comprising: a basic amino acid; from about 50 wt. % to about 80 wt. % water; from about 5 wt. % to about 110 wt. % of a preservative system comprising: benzyl alcohol, benzoic acid or a salt of benzoic acid; and an alkylene glycol.

Further embodiments provide for the use of any one of the compositions described herein for: treating, preventing, reducing the incidence of, or inhibiting dental erosion; treating, preventing, reducing the incidence of, or inhibiting the formation of dental caries; occluding a dentinal tubule; treating, preventing, reducing the incidence of, or inhibiting hypersensitivity of the teeth; fostering growth of beneficial bacteria in the oral cavity; reducing, repairing or inhibiting early enamel lesions, e.g., as detected by quantitative light-induced fluorescence (QLF) or electrical caries measurement (ECM); reducing or inhibiting demineralization and promoting remineralization of the teeth; treating, preventing, reducing the incidence of, or inhibiting gingivitis; promoting healing of sores or cuts in the mouth; reducing levels of acid producing bacteria; increasing relative levels of arginolytic bacteria; inhibiting, microbial bio film formation in the oral cavity; raising and/or maintaining plaque pH at levels of at least pH 5.5 following sugar challenge; reducing plaque accumulation; treating dry mouth; and/or enhancing systemic health, including cardiovascular health, e.g., by reducing potential for systemic infection via the oral tissues.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention therefore provides, in a first embodiment, a mouthwash (Composition 1), comprising a preservative system comprising: benzyl alcohol, benzoic acid or a salt of benzoic acid; and an alkylene glycol.

1.1. Composition 1 further comprising an amino acid selected from lysine, glycine and arginine, in free or orally acceptable acid addition salt form, e.g., hydrochloride form.

1.2. Composition 1 or 1.1 wherein the amino acid is a basic amino acid, e.g., arginine, in free or orally acceptable salt form.

1.3. Any of the foregoing compositions, wherein amino acid is present in an amount of 0.05 to 10 wt. %, e.g., about 1-5 wt. %, optionally 0.1 wt. %, 0.2 wt. %, 0.3 wt. %, 0.4 wt. %, 0.5 wt. %, 0.8 wt. %, 1 wt. %, 2 wt. %, 3 wt. %, 4 wt. %, 5 wt. %.

1.4. Any of the foregoing compositions further comprising an effective amount of a fluoride ion source, e.g., providing 50 to 3000 ppm fluoride, e.g. from about 100 to about 500 ppm, e.g., from about 200 to about 300 ppm e.g. about 225 ppm.

1.5. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.6. Any of the preceding compositions comprising an effective amount of one or more alkali phosphate salts, e.g., sodium, or potassium salts, e.g., selected from alkali dibasic phosphate and alkali pyrophosphate salts, e.g., alkali phosphate salts selected from sodium phosphate dibasic, potassium phosphate dibasic, tetrasodium pyrophosphate, tetrapotassium pyrophosphate, sodium tripolyphosphate, and mixtures of any of two or more of these, e.g., in an amount of 0.1-20%, e.g., 0.25-5%, e.g., 0.25-2%, by weight of the composition.

1.7. Any of the foregoing compositions comprising buffering agents, e.g., sodium phosphate buffer (e.g., sodium phosphate monobasic and disodium phosphate).

1.8. Any of the foregoing compositions comprising a humectant, e.g., selected from glycerin, sorbitol, propylene glycol, polyethylene glycol, xylitol, and mixtures thereof.

1.9. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight, e.g. 1-2% sodium lauryl sulfate (SLS); and/or a zwitterionic surfactant, for example a betaine surfactant, for example cocamidopropylbetaine, e.g. in an amount of from about 0.1% to about 4.5% by weight, e.g. 0.5-2% cocamidopropylbetaine.

1.10. Any of the preceding compositions further comprising hydrogenated castor oil (e.g. from about 0.1-5%, or about 0.5-3%, or about 1-1%).
1.11. Any of the preceding compositions further comprising polyoxyethylene.
1.12. Any of the preceding compositions further comprising sorbitan monolaurate (e.g. Polysorbate 20, e.g. in an amount of 0.1-1 wt. %, or about 0.5 wt. %).
1.13. Any of the preceding compositions further comprising a viscosity modifying amount of one or more of polysaccharide gums, for example xanthan gum or carrageenan, and combinations thereof.
1.14. Any of the preceding compositions further comprising flavoring, fragrance and/or coloring.
1.15. Any of the foregoing compositions comprising an effective amount of one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.
1.16. Any of the preceding compositions further comprising a whitening agent, e.g., a selected from the group consisting of peroxides, metal chlorites, perborates, percarbonates, peroxyacids, and combinations thereof.
1.17. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; sodium perborate, sodium carbonate peroxide, sodium peroxyphosphate, and potassium persulfate);
1.18. Any of the preceding compositions further comprising an agent that interferes with or prevents bacterial attachment, e.g., solbrol or chitosan.
1.19. Any of the preceding compositions further comprising a physiologically or orally acceptable potassium salt, e.g., potassium nitrate or potassium chloride, in an amount effective to reduce dentinal sensitivity.
1.20. Any of the foregoing compositions further comprising an anionic polymer, e.g., a synthetic anionic polymeric polycarboxylate, e.g., wherein the anionic polymer is selected from 1:4 to 4:1 copolymers of maleic anhydride or acid with another polymerizable ethylenically unsaturated monomer; e.g., wherein the anionic polymer is a methyl vinyl ether/maleic anhydride (PVM/MA) copolymer having an average molecular weight (M.W.) of about 30,000 to about 1,000,000, e.g. about 300,000 to about 800,000, e.g., wherein the anionic polymer is about 1-5%, e.g., about 2%, of the weight of the composition.
1.21. Any of the preceding compositions further comprising a breath freshener.
1.22. Any of the foregoing compositions, wherein the pH of the composition is from about 6 to about 10, e.g., about 8 to about 9 (e.g., 7.9 to 8.9), e.g., about 8.5.
1.23. Any of the forgoing compositions for use to reduce and inhibit acid erosion of the enamel, clean the teeth, reduce bacterially-generated biofilm and plaque, reduce gingivitis, inhibit tooth decay and formation of cavities, and reduce dentinal hypersensitivity.

Embodiments of the present invention further provide methods to reduce and inhibit acid erosion of the enamel, clean the teeth, reduce bacterially-generated biofilm and plaque, reduce gingivitis, inhibit tooth decay and formation of cavities, and reduce dentinal hypersensitivity, comprising applying an effective amount of a composition of the invention, e.g., any of Composition 1, et seq. to the teeth.

For example, in various embodiments, the invention provides methods to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; (xv) reduce tartar build-up, and/or (xvi) promote systemic health, including cardiovascular health, e.g., by reducing potential for systemic infection via the oral tissues, comprising applying any of Compositions 1, et seq. as described above to the oral cavity of a person in need thereof, e.g., one or more times per day. The invention further provides Compositions 1, et seq. for use in any of these methods.

Other embodiments comprise an orally acceptable base comprising ingredients selected from one or more of buffering agents, humectants, surfactants, thickeners, breath fresheners, flavoring, fragrance, coloring, antibacterial agents, whitening agents, agents that interfere with or prevent bacterial attachment, phosphate sources, orally acceptable potassium salts, and anionic polymers.

The benefits of the oral care compositions of the invention are numerous. In some embodiments, the oral care compositions provide antimicrobial, antiplaque, antigingivitis, anti-malodor, anticaries, and anticalculus benefits. Additional benefits include but are not limited to anti-attachment, anti-periodontitis and anti-bone loss, as well as promotion of wound healing.

A third benefit is anti-sensitivity benefit as a result of the occlusion. Occlusion of dentin tubules leads to sensitivity relief.

A fourth benefit is the benefit associated with amino acids. The occluding particles and surface deposits contain the corresponding amino acids, such as arginine and lysine.

These amino acids provide multiple benefits. For example, basic amino acids lead to higher pH of the plaque and can provide anticaries benefits.

The zinc ion source may be, e.g., zinc oxide or zinc chloride.

In certain embodiments, zinc is present in an amount of 0.01 to 10% by weight of the composition. In other embodiments, the amount of zinc is at least 0.1, at least 0.2, at least 0.3, at least 0.4, at least 0.5, at least 1, at least 2, at least 3, or at least 4 up to 10% by weight of the composition. In other embodiments, the amount of the zinc is less than 9, less than 8, less than 7, less than 6, less than 5, less than 4, less than 3, less than 2, less than 1, less than 0.5 to 0.05% by weight of the composition. In other embodiments, the amounts are 0.05 to 5%, 0.05 to 4%, 0.05 to 3%, 0.05 to 2%, 0.1 to 5%, 0.1 to 4%, 0.1 to 3%, 0.1 to 2%, 0.5 to 5%, 0.5 to 4%, 0.5 to 3%, or 0.5 to 2% by weight of the composition.

In some embodiments, the total amount of zinc in the composition is 0.05 to 8% by weight of the composition. In other embodiments, the total amount of zinc is at least 0.1, at least 0.2, at least 0.3, at least 0.4, at least 0.5, or at least 1 up to 8% by weight of the composition. In other embodiments, the total amount of zinc in the composition is less than 5, less than 4, less than 3, less than 2, or less than 1 to 0.05% by weight of the composition.

Active Agents:

The compositions of the invention may comprise various agents which are active to protect and enhance the strength and integrity of the enamel and tooth structure and/or to reduce bacteria and associated tooth decay and/or gum disease. Effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 100 ppm, e.g., about 100 to about 2000 ppm, e.g., about 100 to about 1000 ppm, e.g., about 100 to about 500 ppm, e.g., about 200 to about 300 ppm, e.g., about 225 ppm. The appropriate level of fluoride will depend on the particular application. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counterion in the salt.

Amino Acids:

In some embodiments, the compositions of the invention comprise an amino acid. In particular embodiments, the amino acid may be a basic amino acid. By "basic amino acid" is meant the naturally occurring basic amino acids, such as arginine, lysine, and histidine, as well as any basic amino acid having a carboxyl group and an amino group in the molecule, which is water-soluble and provides an aqueous solution with a pH of about 7 or greater. Accordingly, basic amino acids include, but are not limited to, arginine, lysine, citrulline, ornithine, creatine, histidine, diaminobutanoic acid, diaminoproprionic acid, salts thereof or combinations thereof. In a particular embodiment, the basic amino acids are selected from arginine, citrulline, and ornithine.

In various embodiments, the amino acid is present in an amount of about 0.1 wt. % to about 20 wt. % of the total composition weight, about 0.5 wt. % to about 10 wt. % of the total composition weight, for example about 1.5 wt. %, about 3.75 wt. %, about 5 wt. %, or about 7.5 wt. % of the total composition weight in the case of a dentifrice, or for example about 0.5-2 wt. %, e.g., about 1% in the case of a mouthwash.

In certain embodiments, the basic amino acid is arginine, for example, l-arginine, or a salt thereof. Arginine, when present, may be present at levels from, e.g., about 0.1 wt. % to about 20 wt. % (expressed as weight of free base). In some embodiments, arginine is present in an amount of from about 0.1 wt. % to about 10 wt. %, or about 0.25 wt. % to about 8 wt. %, or about 0.5 wt. % to about 4 wt. %, or about 0.75 wt. % to about 1 wt. %, or about 0.8 wt. %.

Foaming Agents:

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. Where present, the amount of of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The compositions useful in the invention may contain anionic surfactants, for example:
i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate,
ii. higher alkyl sulfates, such as sodium lauryl sulfate,
iii. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K, for example sodium laureth-2 sulfate $(CH_3(CH_2)_{10}CH_2(OCH_2CH_2)_2OSO_3Na)$.
iv. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., $C_{6-30}$ alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Tartar Control Agents:

In various embodiments of the present invention, the compositions comprise an anticalculus (tartar control) agent. Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. The invention thus may comprise phosphate salts. In particular embodiments, these salts are alkali phosphate salts, i.e., salts of alkali metal hydroxides or alkaline earth hydroxides, for example, sodium, potassium or calcium salts. "Phosphate" as used herein encompasses orally acceptable mono- and polyphosphates, for example, $P_{1-6}$ phosphates, for example monomeric phosphates such as monobasic, dibasic or tribasic phosphate; dimeric phosphates such as pyrophosphates; and multimeric phosphates, e.g., sodium hexametaphosphate. In particular examples, the selected phosphate is selected from alkali dibasic phosphate and alkali pyrophosphate salts, e.g., selected from sodium phosphate dibasic, potassium phosphate dibasic, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), and sodium phosphate dibasic ($Na_2HPO_4$), e.g., in amounts of ca. 3-4% of the sodium phosphate dibasic and ca. 0.2-1% of each of the pyrophosphates. In another embodiment, the compositions comprise a mixture of tetrasodium pyrophosphate (TSPP) and sodium tripolyphosphate (STPP) ($Na_5P_3O_{10}$), e.g., in proportions of TSPP at about 1-2% and STPP at about 7% to about 10%. Such phosphates are provided in an amount effective to reduce erosion of the enamel, to aid in cleaning the teeth, and/or to reduce tartar buildup on the teeth, for example in an amount of 2-20%, e.g., ca. 5-15%, by weight of the composition.

Flavoring Agents:

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.01 to about 5% by weight, e.g. about 0.05 to about 1.5%, e.g. about 0.1 to about 1%, by weight.

Polymers:

The oral care compositions of the invention may also include polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Some embodiments of the present invention comprise a thickening agent selected from: carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. In certain embodiments, thickening agents in an amount of about 0.5% to about 5.0% by weight of the total composition are used.

The compositions of the invention may include an anionic polymer, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid. Another useful class of polymeric agents includes polyamino acids containing proportions of anionic surface-active amino acids such as aspartic acid, glutamic acid and phosphoserine, e.g. as disclosed in U.S. Pat. No. 4,866,161 Sikes et al.

Water:

The oral compositions may comprise significant levels of water. Water employed in the preparation of commercial oral compositions should be deionized and free of organic impurities. The amount of water in the compositions includes the free water which is added plus that amount which is introduced with other materials. In some embodiments, the compositions of the present invention comprise greater than 50 wt. % water. In other embodiments, the compositions of the present invention comprise from about 50 wt. % to about 95 wt. % water. Still further embodiments provide compositions comprising from about 55 wt. % to about 70 wt. % water. While other embodiments provide compositions comprising from about 57.5 wt. % water to about 62.5 wt. % water. In some embodiments, the compositions of the present invention comprise from about 58 wt. % to about 60 wt. % water.

Humectants:

Within certain embodiments of the oral compositions, it is also desirable to incorporate a humectant to prevent the composition from hardening upon exposure to air. Certain humectants can also impart desirable sweetness or flavor to dentifrice compositions. Suitable humectants include edible polyhydric alcohols such as glycerin, sorbitol, xylitol, propylene glycol as well as other polyols and mixtures of these humectants. In some embodiments, the principal humectant is glycerin, which may be present at levels of from about 10% to about 25%, e.g. 15-20%, or about 18%, by weight. Other embodiments comprise sorbitol, e.g., from about 5% to about 10%, e.g., about 7%, by weight. Further embodiments provide a humectant combination comprising glycerin and sorbitol.

Other Optional Ingredients:

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Unless stated otherwise, all percentages of composition components given in this specification are by weight based on a total composition or formulation weight of 100%.

Unless otherwise specifically identified, the ingredients for use in the compositions and formulations of the present invention are preferably cosmetically acceptable ingredients. By "orally acceptable" is meant suitable for use in a formulation for application to the oral cavity of a mammal. An orally acceptable excipient, for example, is an excipient which is suitable for administration to the oral cavity in the amounts and concentrations contemplated in the formulations of this invention, and includes for example excipients which are "Generally Recognized as Safe" (GRAS) by the United States Food and Drug Administration.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Described below are exemplary compositions of the present invention and several comparative compositions which do not include the inventive preservative systems described herein.

TABLE 1

| Ingredients | Std | 1 | 2 | 3 | 4 | 5 Wt. % | 6 | 7 | 8 | 9 | 10 |
|---|---|---|---|---|---|---|---|---|---|---|---|
| Water | 62.34 | 62.25 | 62.15 | 62.05 | 61.95 | 61.95 | 62.14 | 59.15 | 59.15 | 59.25 | 62.25 |
| Propylene Glycol | 4 | 4 | 4 | 4 | 4 | 4 | 4 | 7 | 4 | 7 | 4 |
| Methylisothiazolinone | 0.01 | — | — | — | — | — | — | — | — | — | — |
| Benzyl Alcohol | 0.1 | 0.2 | 0.3 | 0.4 | 0.3 | 0.3 | 0.3 | 0.3 | 0.2 | 0.2 | 0.2 |
| Caprylyl Glycol | — | — | — | — | 0.2 | — | — | — | 0.2 | — | — |
| Hexanediol + Caprylyl Glycol | — | — | — | — | — | 0.2 | — | — | — | — | — |
| Cetylpyridinium Chloride | — | — | — | — | — | — | 0.015 | — | — | — | — |
| Glycerin | 18 | 18 | 18 | 18 | 18 | 18 | 18 | 18 | 18 | 18 | 18 |
| Sorbitol | 7 | 7 | 7 | 7 | 7 | 7 | 7 | 7 | 7 | 7 | 7 |
| Flavor A | 0.2 | 0.2 | 0.2 | 0.2 | 0.2 | 0.2 | 0.2 | 0.2 | 0.2 | 0.2 | — |
| Flavor B | — | — | — | — | — | — | — | — | — | — | 0.2 |
| L-arginine | 0.8 | 0.8 | 0.8 | 0.8 | 0.8 | 0.8 | 0.8 | 0.8 | 0.8 | 0.8 | 0.8 |
| Others (e.g. anti-calculus agents, antibacterial agents, anti-sensitivity agents, thickeners, etc.) | QS | QS | QS | QS | QS | QS | QS | QS | QS | QS | QS |

Std = currently marketed formula

The compositions described in Table 1 (above) can be prepared by methods generally known to those skilled in the art.

Example 2

Tests are performed to determine the antimicrobial preservation effectiveness of various compositions. Compositions are inoculated with mixed species of microorganisms of known quantities (bacterial and fungal) and monitored for survival every 7 days over a four-week interval. The results of these tests are described below in Table 2.

TABLE 2

| Composition | Log Reduction for mold Aged* APET(*4 weeks) |
|---|---|
| Control | 2.3 |
| 1 | 2 |
| 2 | 2.6 |
| 3 | 3.9 |
| 4 | 4.9 |
| 5 | 4.9 |
| 6 | 4.9 |
| 7 | 4.9 |

The data described in Table 2 (above) demonstrates that certain preservative systems more effectively inhibit microorganism growth, than others.

Example 3

Flavor evaluations of various compositions are performed by an expert panel. The results of these evaluations are described below in Table 3.

TABLE 3

| Composition | Pass/Fail | Comments |
|---|---|---|
| Control | Pass | None |
| 1 | Pass | Similar to Control |
| 2 | Fail | Metallic aftertaste, bitter and tingling |
| 3 | Fail | Metallic aftertaste, much more tingling than Control |

TABLE 3-continued

| Composition | Pass/Fail | Comments |
|---|---|---|
| 4 | Fail | Slight metallic and waxy aftertaste, less bitter than 2 or 3 |
| 5 | Fail | Metallic, waxy and rancid aftertaste, off notes, tingling |
| 6 | Fail | Metallic aftertaste and tingling |
| 7 | Fail | Metallic aftertaste and tingling |

As illustrated by the results described in Table 3 (above), preservative systems can have a significant impact on the flavor profile of a composition; and finding a combination of ingredients that provides an acceptable level of preservation, as well as an acceptable flavor profile, is challenging.

Example 4

Compositions 1, 8, 9 and 10 are further evaluated in a second-level flavor screening. The compositions are aged at 40° C. and 75% relative humidity (RH) and evaluated after eight weeks. The results of this second-level flavor screen are described below in Table 4.

TABLE 4

| Composition | Comments |
|---|---|
| 1 | Bitter aftertaste |
| 8 | Waxy aftertaste |
| 9 | Excellent flavor impact and long-lasting |
| 10 | Bitter and waxy aftertaste |

The results described in Table 4 (above) demonstrate that the inventive preservation systems of the claimed invention also provide an unexpectedly superior taste profile.

Example 5

A cosmetic evaluation is performed on the compositions that passed the flavor screen (Compositions 1, 8 and 10), and a fourth composition comprising 0.2 wt. % benzyl alcohol and 7 wt. % propylene glycol (Composition 9). Specifically, the visual appearance and color of these compositions are evaluated after four weeks at 40° C. and 49° C. The results of these evaluations are described in Table 5 (below).

TABLE 5

| Composition | Appearance | Color |
|---|---|---|
| 1 | Phase separation/cloudiness after four weeks at 49° C. | Yellowish |
| 8 | Phase separation/cloudiness after four weeks at 49° C. | Yellowish |
| 9 | Pass | No color change |
| 10 | Pass | Yellowish |

The results described in Table 5 (above) demonstrate that exemplary compositions of the present invention comprising an exemplary preservative system of the claimed invention were cosmetically stable after four weeks at elevated temperatures.

Example 6

The compositions evaluated in Examples 4 and 5 (Compositions 1, 8, 9 and 10) are further evaluated in an adequacy of preservation test similar to the evaluation performed in Example 2, wherein the compositions are evaluated for microorganism growth after twenty-eight days. The results of these evaluations are described in Table 6 (below).

TABLE 6

| Composition | Log Reduction for mold Aged* APET(*13 weeks) |
|---|---|
| 1 | 1.8 |
| 8 | 3.4 |
| 9 | 3.6 |
| 10 | 1.7 |

As illustrated by the data described in Table 6 (above), an exemplary preservative system of the present invention was able to provide a superior level of microorganism inhibition.

In summary, the data described in the Examples section underscores the inventiveness of the compositions and preservative systems of the present invention. In particular, it was truly unexpected that the preservative systems of the present invention were able to provide the observed microbial and fungal inhibition, and also provide an appealing flavor profile and long-term stability to high-water compositions.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the scope of the invention should be construed broadly as set forth in the appended claims.

What is claimed is:

1. A mouthwash comprising:
   from 0.5-2% by wt. arginine, in free or salt form;
   from about 50 wt. % to about 80 wt. % water;
   0.2 wt % benzyl alcohol;
   7 wt % propylene glycol;
   7 wt % sorbitol;
   a methyl vinyl ether/maleic anhydride copolymer having a molecular weight (M.W.) of from about 300,000 to about 800,000; and
   18 wt % glycerin.

2. A method for:
   treating, preventing, reducing the incidence of, or inhibiting dental erosion;
   treating, preventing, reducing the incidence of, or inhibiting the formation of dental caries;
   occluding a dentinal tubule;
   treating, preventing, reducing the incidence of, or inhibiting hypersensitivity of the teeth;
   fostering growth of beneficial bacteria in the oral cavity;
   reducing, repairing or inhibiting early enamel lesions;
   reducing or inhibiting demineralization and promoting remineralization of the teeth;
   treating, preventing, reducing the incidence of, or inhibiting gingivitis;
   promoting healing of sores or cuts in the mouth;
   reducing levels of acid producing bacteria;
   increasing relative levels of arginolytic bacteria;
   inhibiting microbial bio film formation in the oral cavity;
   raising and/or maintaining plaque pH at levels of at least pH 5.5 following sugar challenge;
   reducing plaque accumulation;
   treating dry mouth; and/or
   enhancing systemic health, including cardiovascular health;
   comprising: administering an oral care composition according to claim 1 to a subject in need thereof.

3. The method according to claim 2, wherein about twenty milliliters (20 ml) of the oral care composition is administered to the oral cavity, swished for about 30 seconds and then expectorated.

4. The mouthwash according to claim 1, further comprising hydrogenated castor oil.

5. The mouthwash according to claim 1, further comprising one or more alkali phosphate salts.

6. The mouthwash according to claim 1, further comprising sorbitan monolaurate.

* * * * *